(12) United States Patent
Karunasiri et al.

(10) Patent No.: US 7,777,641 B2
(45) Date of Patent: Aug. 17, 2010

(54) SYSTEMS AND METHODS OF FACILITATING COMMUNICATION BETWEEN A FIRST AND SECOND DEVICE

(75) Inventors: Rankiri T. Karunasiri, Castaic, CA (US); Diane H. Chang, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 1176 days.

(21) Appl. No.: 11/393,449

(22) Filed: Mar. 29, 2006

(65) Prior Publication Data

US 2007/0250136 A1 Oct. 25, 2007

(51) Int. Cl.
*G05B 19/02* (2006.01)
(52) U.S. Cl. ............... 340/825.22; 340/3.1; 340/5.1
(58) Field of Classification Search ............ 340/825.22, 340/825.2, 3.1, 5.1; 326/80, 88, 92
See application file for complete search history.

(56) References Cited

U.S. PATENT DOCUMENTS

| | | | |
|---|---|---|---|
| 3,760,984 A | 9/1973 | Theeuwes | |
| 3,987,790 A | 10/1976 | Eckenhoff et al. | |
| 3,995,631 A | 12/1976 | Higuchi et al. | |
| 4,008,429 A * | 2/1977 | Phalan | 323/222 |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,400,590 A | 8/1983 | Michelson | |
| 4,487,603 A | 12/1984 | Harris | |
| 4,491,743 A * | 1/1985 | Smith | 326/75 |
| 4,532,930 A | 8/1985 | Crosby et al. | |
| 4,562,751 A | 1/1986 | Nason et al. | |
| 4,578,601 A * | 3/1986 | McAlister et al. | 326/72 |
| 4,592,359 A | 6/1986 | Galbraith | |

(Continued)

*Primary Examiner*—Vernal U Brown
(74) *Attorney, Agent, or Firm*—AdvantEdge Law Group, LLC

(57) ABSTRACT

Systems for facilitating communication between a first and second device include a voltage level translator circuit configured to convert a voltage level of one or more digital signals that are transmitted from the first device to the second device to a voltage level substantially equal to a supply voltage level of the second device. The conversion is based on a first input voltage signal into the translator circuit. The systems further include a diode in series with a capacitor. The diode is configured to generate the first input voltage signal by charging the capacitor to a voltage level that is substantially equal to the voltage level of the one or more digital signals. Methods of facilitating communication between a first and second device include providing a voltage level translator circuit configured to convert a voltage level of one or more digital signals that are transmitted from the first device to the second device to a voltage level substantially equal to a supply voltage level of the second device. The conversion is based on a first input voltage signal into the translator circuit. The methods further include providing a circuit comprising a diode in series with a capacitor and generating the first input voltage signal by charging the capacitor to a voltage level that is substantially equal to the voltage level of the one or more digital signals.

20 Claims, 6 Drawing Sheets

U.S. PATENT DOCUMENTS

| | | |
|---|---|---|
| 4,627,850 A | 12/1986 | Deters et al. |
| 4,678,408 A | 7/1987 | Nason et al. |
| 4,685,903 A | 8/1987 | Cable et al. |
| 4,692,147 A | 9/1987 | Duggan |
| 4,725,852 A | 2/1988 | Gamblin et al. |
| 4,819,647 A | 4/1989 | Byers et al. |
| 4,865,845 A | 9/1989 | Eckenhoff et al. |
| 4,947,844 A | 8/1990 | McDermott |
| 5,057,318 A | 10/1991 | Magruder et al. |
| 5,059,423 A | 10/1991 | Magruder et al. |
| 5,080,653 A | 1/1992 | Voss et al. |
| 5,097,122 A | 3/1992 | Colman et al. |
| 5,112,614 A | 5/1992 | Magruder et al. |
| 5,137,727 A | 8/1992 | Eckenhoff |
| 5,193,539 A | 3/1993 | Schulman et al. |
| 5,193,540 A | 3/1993 | Schulman et al. |
| 5,234,692 A | 8/1993 | Magruder et al. |
| 5,234,693 A | 8/1993 | Magruder et al. |
| 5,312,439 A | 5/1994 | Loeb |
| 5,501,703 A | 3/1996 | Holsheimer |
| 5,728,396 A | 3/1998 | Peery et al. |
| 5,824,022 A | 10/1998 | Zilberman et al. |
| 5,938,688 A | 8/1999 | Schiff |
| 5,963,054 A * | 10/1999 | Cochran et al. ............... 326/68 |
| 6,016,449 A | 1/2000 | Fischell et al. |
| 6,051,017 A | 4/2000 | Loeb et al. |
| 6,129,753 A | 10/2000 | Kuzma |
| 6,164,284 A | 12/2000 | Schulman et al. |
| 6,185,452 B1 | 2/2001 | Schulman et al. |
| 6,208,894 B1 | 3/2001 | Schulman et al. |
| 6,219,580 B1 | 4/2001 | Faltys et al. |
| 6,272,382 B1 | 8/2001 | Faltys et al. |
| 6,308,101 B1 | 10/2001 | Faltys et al. |
| 6,368,315 B1 | 4/2002 | Gillis et al. |
| 6,381,496 B1 | 4/2002 | Meadows et al. |
| 6,487,446 B1 | 11/2002 | Hill et al. |
| 6,516,227 B1 | 2/2003 | Meadows et al. |
| 6,553,263 B1 | 4/2003 | Meadows et al. |
| 6,620,151 B2 | 9/2003 | Blischak et al. |
| 6,666,845 B2 | 12/2003 | Hooper et al. |
| 6,740,072 B2 | 5/2004 | Starkweather et al. |
| 6,760,626 B1 | 7/2004 | Boveja |
| 6,770,067 B2 | 8/2004 | Lorenzen et al. |

* cited by examiner

SYSTEMS AND METHODS OF FACILITATING COMMUNICATION BETWEEN A FIRST AND SECOND DEVICE

BACKGROUND

It is often desirable for electronic devices to transmit data, transfer power, or otherwise communicate one with another. For example, a microprocessor is often configured to transmit data to and receive data from a peripheral device such as a flash memory device.

Reliable communication is especially important in medical devices, where miscommunication may result in device malfunction and harm to a patient. For example, many implantable medical devices, such as implantable stimulators, are configured to transmit status updates to and receive operational instructions and power from one or more external devices. Without accurate communication, these implantable medical devices could cease to function properly.

An exemplary implantable medical device is an implantable cochlear stimulator (ICS), which may be used to treat sensorineural hearing loss. An ICS seeks to bypass the hair cells in the cochlea, which are essential to hearing but which may not be functioning properly, by presenting electrical stimulation directly to the auditory nerve fibers. This leads to the perception of sound in the brain and at least partial restoration of hearing function.

A typical ICS is intended to remain permanently in the body of a patient once it is implanted. For this reason, a behind-the-ear (BTE) signal processor may be positioned behind the ear and used to support the ICS by transmitting various stimulation parameters to the ICS, receiving status data from the ICS, and/or providing power to the ICS.

It is often desirable to modify the stimulation parameters that are transmitted to an ICS by a BTE signal processor or otherwise program the BTE signal processor. To this end, a clinician's programming interface (CPI) is often used. A CPI is a device that allows a programming device (e.g., a personal computer or the like) to interface with a BTE processor. The CPI is typically connected to a BTE with a programming cable.

The same CPI is often used to facilitate the programming of many different types of BTE processors. However, the CPI and each BTE processor may be configured to operate using different supply voltages. For example, a typical CPI operates at 3.0 volts while some BTE processors operate at 2.0 volts and others at 2.7 volts. However, optimal communication between two devices occurs when both devices are operating at the same voltage level. Hence, the difference in supply voltages between the CPI and the BTE processors makes it difficult for accurate communication to occur therebetween.

The above example is typical of many different instances where communication between two devices is sub-optimal or impossible due to differences in supply voltage levels. Various arrangements are currently used to facilitate communication between devices having different having different supply voltage levels. However, many of these arrangements have a number of drawbacks.

For example, to facilitate communication between a CPI and a BTE processor, the programming cable that couples the two devices may include circuitry that converts one supply voltage level to the other. However, if the same CPI is used to program multiple BTE processors each operating at different voltage levels, this approach would require different programming cables to be used for each BTE processor. The use of multiple programming cables is often undesirable because of cost, complexity, and the potential for confusion.

SUMMARY

Systems for facilitating communication between a first and second device include a voltage level translator circuit configured to convert a voltage level of one or more digital signals that are transmitted from the first device to the second device to a voltage level substantially equal to a supply voltage level of the second device. The conversion is based on a first input voltage signal into the translator circuit. The systems further include a diode in series with a capacitor. The diode is configured to generate the first input voltage signal by charging the capacitor to a voltage level that is substantially equal to the voltage level of the one or more digital signals.

Methods of facilitating communication between a first and second device include providing a voltage level translator circuit configured to convert a voltage level of one or more digital signals that are transmitted from the first device to the second device to a voltage level substantially equal to a supply voltage level of the second device. The conversion is based on a first input voltage signal into the translator circuit. The methods further include providing a circuit comprising a diode in series with a capacitor and generating the first input voltage signal by charging the capacitor to a voltage level that is substantially equal to the voltage level of the one or more digital signals.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Systems and methods of facilitating communication between a first and second device operating at different voltage levels are described herein. A voltage level translator circuit requiring first and second input voltage signals is configured to convert a voltage level of one or more digital signals that are transmitted from the first device to the second device to a voltage level substantially equal to a supply voltage level of the second device. The first input voltage signal is derived from one of the digital signals transmitted from the first device to the second device by charging a capacitor with a diode to a voltage level that is substantially equal to the voltage level of the one or more digital signals. The second input voltage signal may be input directly from the power supply of the second device.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

The methods and systems described herein may be used to facilitate communication between any two devices. However, for illustrative purposes only, the present methods and systems will be described in the context of a clinician's programming interface (CPI) and a behind the ear (BTE) signal processor used in connection with a cochlear implant system.

To facilitate an understanding of the methods and systems described herein, an exemplary cochlear implant system will be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; and 5,824,022; 6,219,580; 6,272,382; and 6,308,101. All of these listed patents are incorporated herein by reference in their respective entireties.

Figure 1:
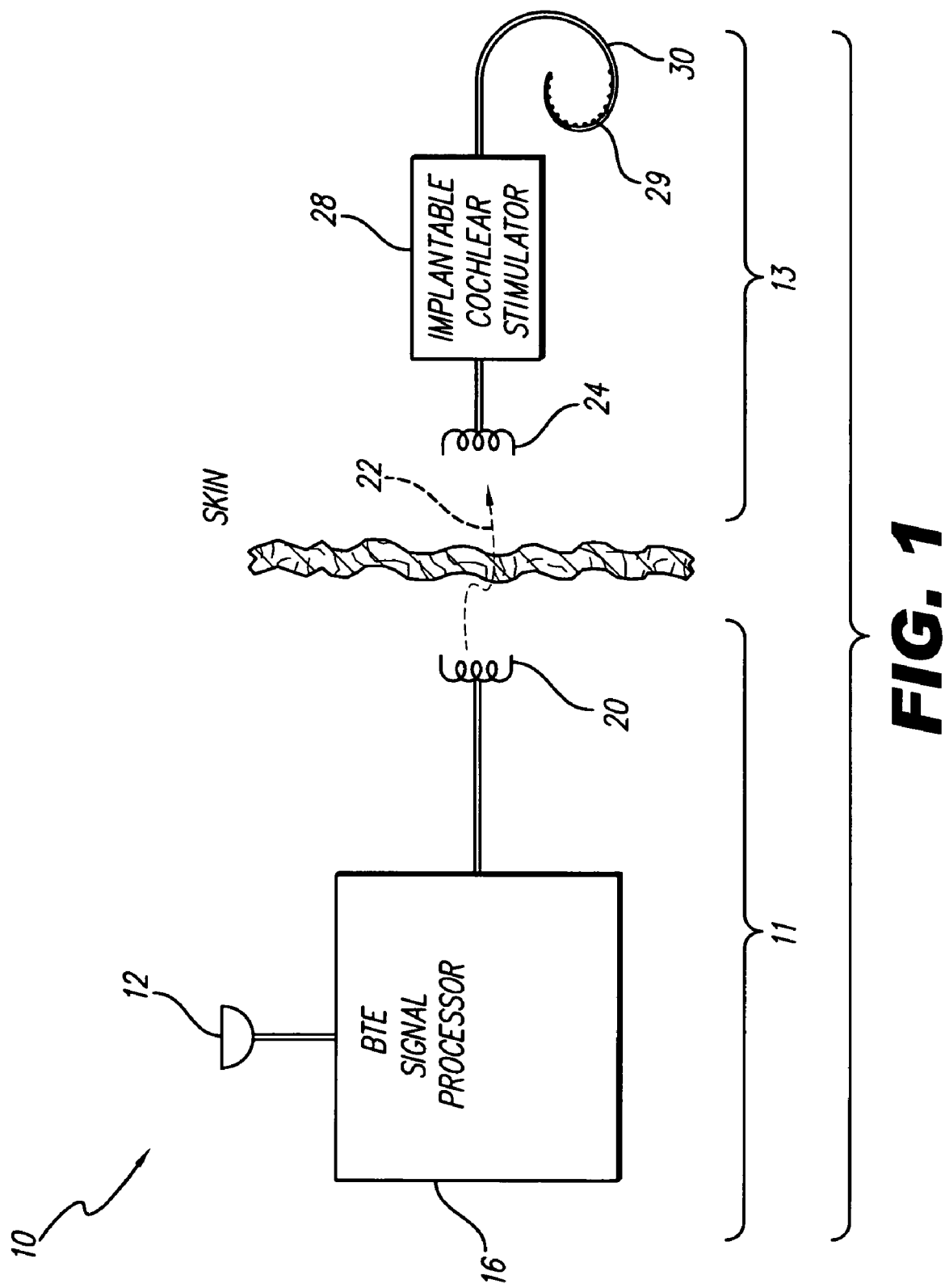
FIG. 1 illustrates an exemplary cochlear implant system according to principles described herein.

As shown in FIG. 1, the cochlear implant system (10) includes an external signal processor portion (11) and a implanted cochlear stimulation portion (13). The signal processor portion (11) may include a BTE signal processor (16), a microphone (12), and/or additional circuitry as best serves a particular application. The cochlear stimulation portion (13) may include an implantable cochlear stimulator (ICS) (28), a number of electrodes (29) disposed on a lead (30), and/or additional circuitry as best serves a particular application. The components within the signal processor portion (11) and the cochlear stimulation portion (13) will be described in more detail below.

The microphone (12) of FIG. 1 is configured to sense acoustic signals and convert such sensed signals to corresponding electrical signals. The electrical signals are sent to the BTE processor (16) over an electrical or other suitable link. Alternatively, the microphone (12) may be connected directly to, or integrated with, the BTE processor (16). The BTE processor (16) processes these converted acoustic signals in accordance with a selected speech processing strategy to generate appropriate control signals or stimulation parameters for controlling the ICS (28). These stimulation parameters may specify or define the polarity, magnitude, location (i.e., which electrode pair or electrode group receive the stimulation current), and timing (i.e., when the stimulation current is to be applied to a particular electrode pair) of the stimulation current that is generated by the ICS (28).

The lead (30) of FIG. 1 is adapted to be inserted within a duct of the cochlea. As shown in FIG. 1, the lead (30) includes a multiplicity of electrodes (29), e.g., sixteen electrodes, disposed along its length. Each of the electrodes (29) is individually coupled to the ICS (28). The lead (30) may be substantially as shown and described in U.S. Pat. Nos. 4,819,647 or 6,129,753, each of which is incorporated herein by reference in its respective entirety. Electronic circuitry within the ICS (28) is configured to apply stimulation current to selected pairs or groups of the individual electrodes (29) included within the lead (30) in accordance with a specified stimulation pattern controlled by the BTE processor (16).

As mentioned, the ICS (28) and lead (30) may be implanted within the patient while the BTE processor (16) and the microphone (12) are configured to be located outside the patient, e.g., behind the ear. Hence, the ICS (28) and the BTE processor (16) may be transcutaneously coupled via a suitable data or communications link (22). The communications link (22) allows power and control signals to be sent from the BTE processor (16) to the ICS (28). In some embodiments, data and status signals may also be sent from the ICS (28) to the BTE processor (16).

The external and implantable portions of the cochlear implant system (10) may each include one or more coils configured to transmit and receive power and/or control signals via the data link (22). For example, the external portion (11) of the cochlear implant system (10) may include an external coil (20) and the implantable portion of the cochlear implant system (13) may include an implantable coil (24). The external coil (20) and the implantable coil (24) may be inductively coupled to each other, thereby allowing data and power signals to be wirelessly transmitted between the external portion and the implantable portion of the cochlear implant system (10).

Figure 2:
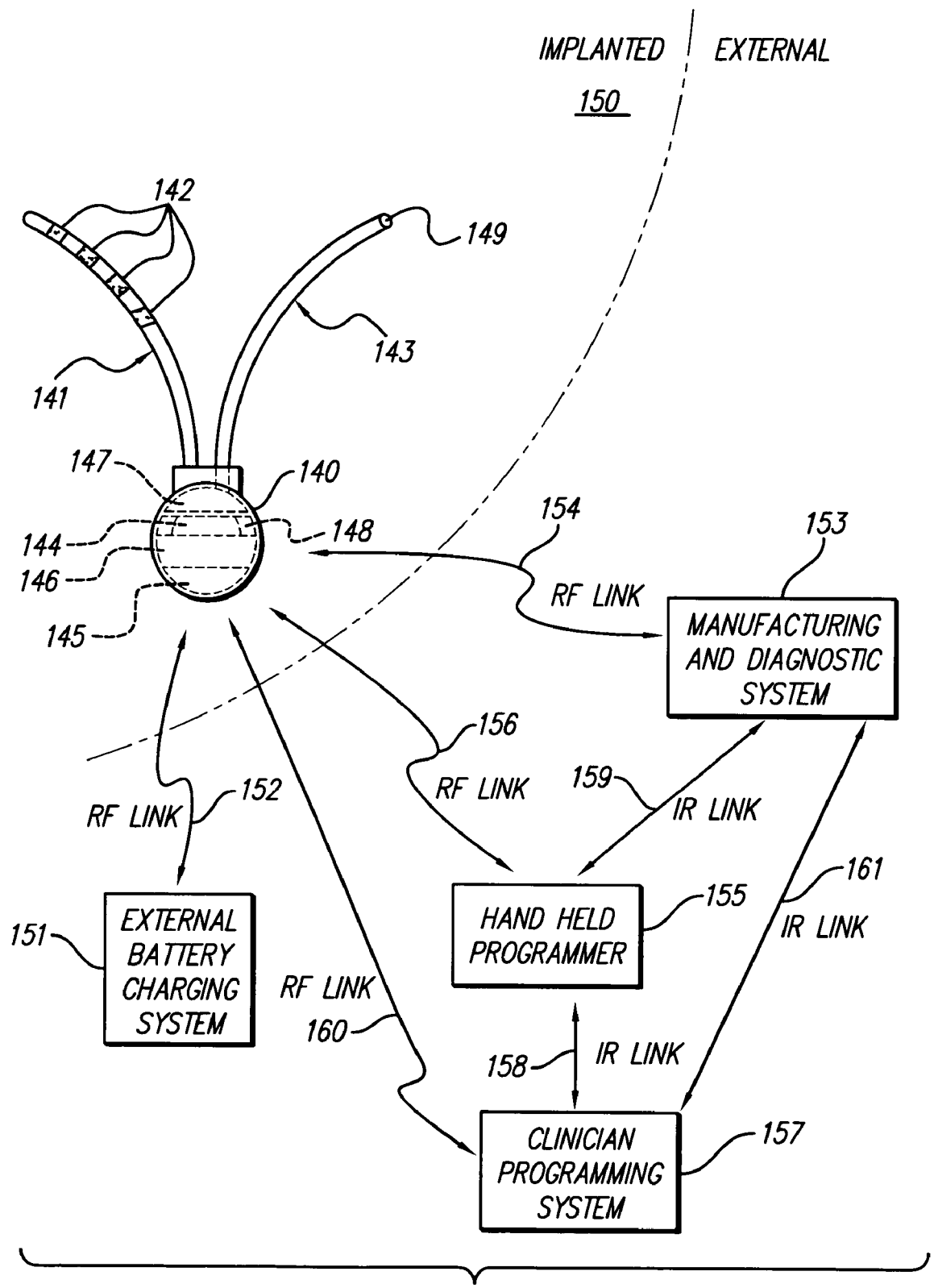
FIG. 2 illustrates an exemplary implantable stimulator according to principles described herein.

The cochlear implant system (10) described in connection with FIG. 1 is merely illustrative of the many types of stimulators that may be used to apply a stimulus to one or more stimulation sites within a patient to treat a wide variety of medical conditions. For example, FIG. 2 illustrates an exemplary stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 2 is configured to provide electrical stimulation to a stimulation site within a patient and may include a lead (141) having a proximal end coupled to the body of the stimulator (140). The lead (141) also includes a number of electrodes (142) configured to apply an electrical stimulation current to a stimulation site. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) maybe thin (e.g., less than 3 millimeters in diameter) such that the lead (141) may be positioned near a stimulation site. In some alternative examples, the stimulator (140) is leadless.

As illustrated in FIG. 2, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

The stimulator (140) may also include a coil (148) configured to receive and/or emit a magnetic field (also referred to as a radio frequency (RF) field) that is used to communicate with, or receive power from, one or more external devices (e.g., 151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

Additionally, if multiple external devices are used in the treatment of a patient, there may be some communication among those external devices, as well as with the implanted stimulator (140) and/or other implanted devices. Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) maybe performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate stimulation pulses in accordance with the stimulation parameters. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

Additionally, the exemplary stimulator (140) shown in FIG. 2 is configured to provide drug stimulation to a patient by applying one or more drugs at a stimulation site within the patient. Hence, to facilitate drug stimulation, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. For example, the pump (147) may include a reservoir configured to hold one or more drugs. In some examples, the volume of the reservoir is sufficiently large so as to contain enough drugs for the patient's anticipated lifetime. Alternatively, the reservoir may be refillable, e.g., through a percutaneous injection with a hypodermic needle.

Controlled drug release devices based upon a mechanical or electromechanical infusion pump may be alternatively used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760, 984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234, 692; 5,234,693; 5,728,396; 6,368,315; 6,666,845; and 6,620, 151. All of these listed patents are incorporated herein by reference in their respective entireties.

Hence, as used herein, and in the appended claims, the term "stimulator" will be used broadly to refer to any device that delivers a stimulus, such as an electrical stimulation current, one or more drugs or other chemical stimulation, thermal stimulation, electromagnetic stimulation, mechanical stimulation, gene infusion, and/or any other suitable stimulation at a stimulation site to treat a psychotic disorder. Thus, the term "stimulator" includes, but is not limited to, a cochlear implant system, stimulator, microstimulator, implantable pulse generator (IPG), spinal cord stimulator (SCS), system control unit, deep brain stimulator, drug pump, or similar device.

Exemplary implantable microstimulators, such as the BION® microstimulator (manufactured by Advanced Bionics® Corporation, Valencia, Calif.), suitable for use as described herein include, but are not limited to, those disclosed in U.S. Pat. Nos. 5,193,539; 5,193,540; 5,312,439; 6,185,452; 6,164,284; 6,208,894; and 6,051,017. Exemplary IPGs suitable for use as described herein include, but are not limited to, those disclosed in U.S. Pat. Nos. 6,381,496, 6,553, 263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539, 263. All of these listed patents are incorporated herein by reference in their respective entireties.

Any of the external devices shown in FIGS. 1-2 (e.g., the BTE signal processor (16; FIG. 1), EBCS (151; FIG. 2), or hand held programmer (HHP) (155; FIG. 2)) may be coupled to another external device and configured to communicate with that device. For example, and as mentioned previously, a clinician's programming interface (CPI) is often coupled to and used to facilitate programming of a BTE processor (16; FIG. 1).

Figure 3:
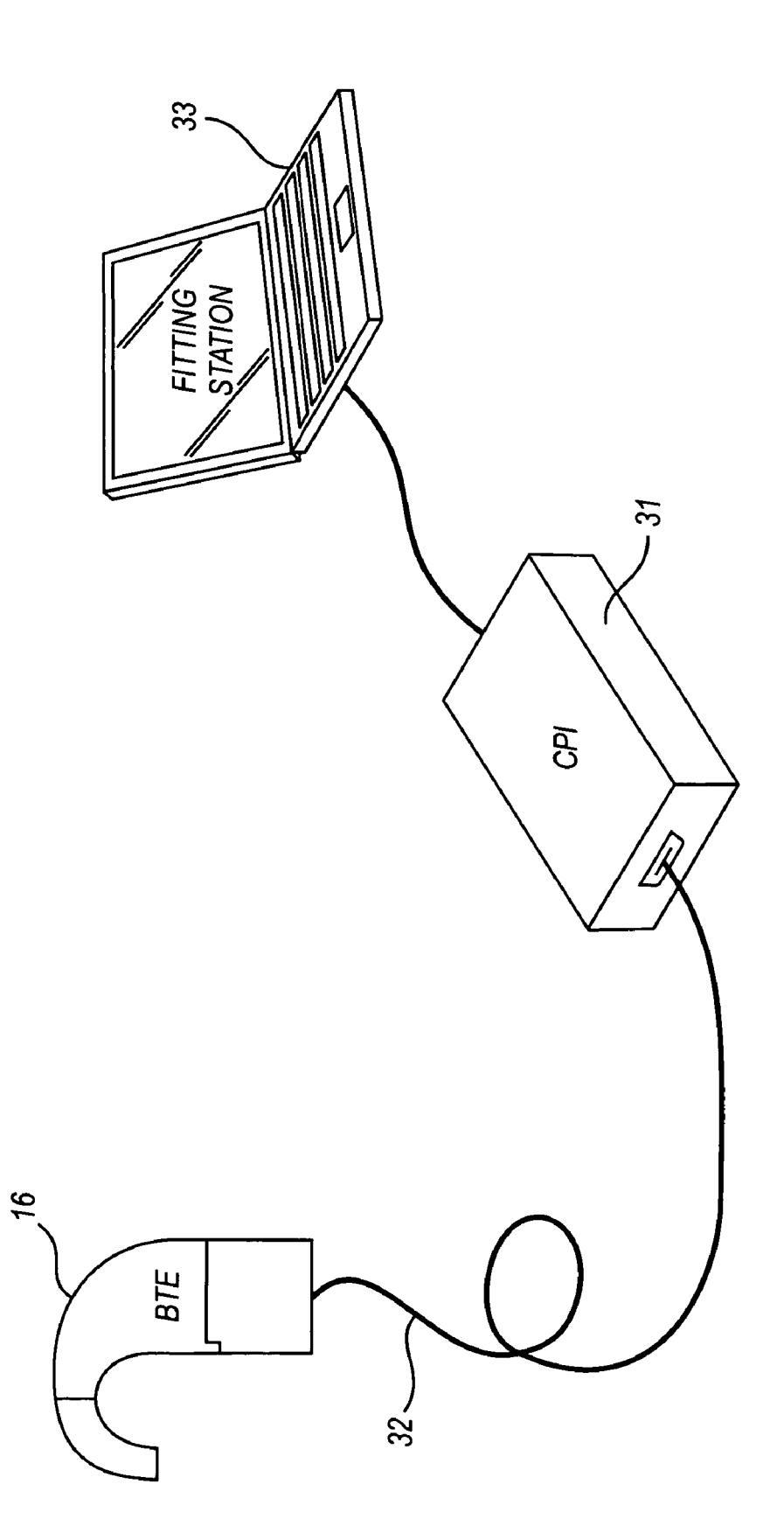
FIG. 3 illustrates an exemplary system wherein a clinician's programming interface (CPI) is coupled to a behind-the-ear (BTE) processor via a programming cable according to principles described herein.

FIG. 3 illustrates an exemplary system wherein a CPI (31) is coupled to a BTE processor (16) via a programming cable (32). As shown in FIG. 3, the CPI (31) is also coupled to a fitting station (33). The fitting station (33) may be used by a clinician to program or fit the BTE processor (16) to a particular patient.

Figure 4:
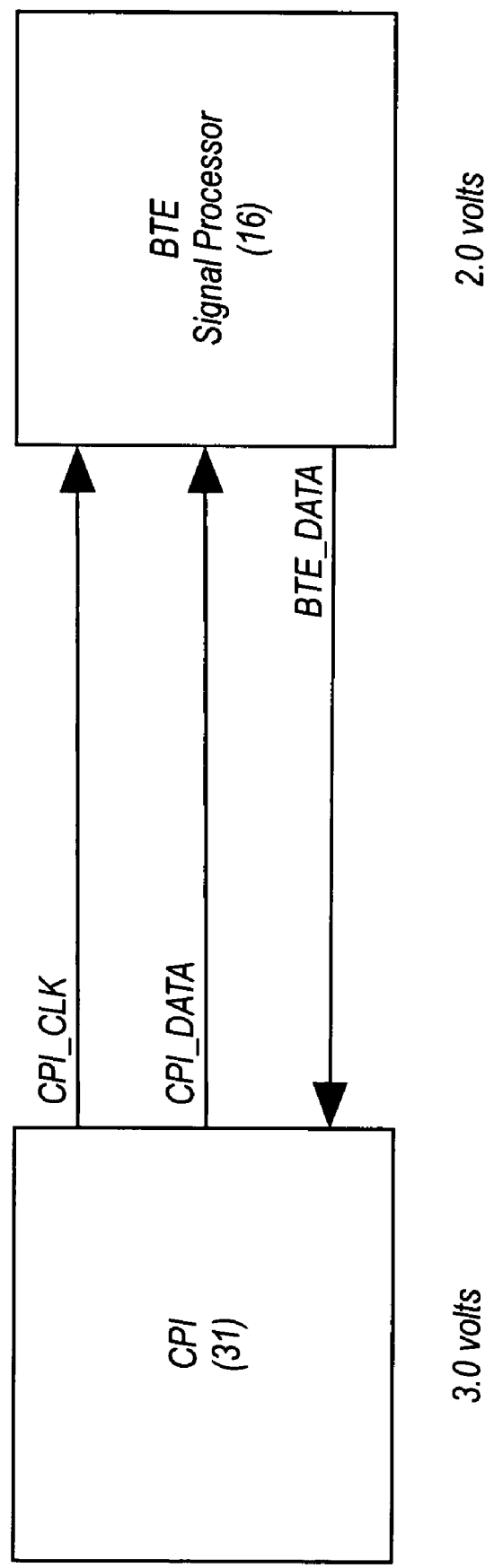
FIG. 4 is a block diagram illustrating a number of exemplary signals that may be transmitted between the CPI and BTE processor according to principles described herein.

FIG. 4 is a block diagram illustrating a number of exemplary signals that may be transmitted between the CPI (31) and BTE processor (16). The signals shown in FIG. 4 are merely illustrative of the many different signals that may be transmitted between the two devices. It will be recognized that any other signal may be transmitted as best serves a particular application.

As shown in FIG. 4, a clock signal labeled CPI_CLK may be transmitted from the CPI (31) to the BTE processor (16). CPI_CLK is a square wave, for example, and may have any suitable frequency as best serves a particular application. An exemplary frequency of CPI_CLK is 250 KHz. Another signal, labeled CPI_DATA in FIG. 4, may be transmitted from the CPI (31) to the BTE processor (16). CPI_DATA may include any data, such as, but not limited to, stimulation parameter data or any other type of programming data.

Likewise, data may be transmitted from the BTE processor (16) to the CPI (31). For example, as shown in FIG. 4, a signal labeled BTE_DATA may be transmitted from the BTE processor (16) to the CPI (31). BTE_DATA may include any type of data, such as, but not limited to, data detailing the status and/or performance of the BTE processor (16) and/or the implantable cochlear stimulator (28; FIG. 1).

As mentioned, the CPI (31) and BTE processor (16) often operate using different supply voltage levels. For example, the CPI (31) shown in FIG. 3 operates at 3.0 volts while the BTE processor (16) operates at 2.0 volts. It will be recognized that the CPI (31) and/or the BTE processor (16) may be configured to operate at any voltage level as best serves a particular application.

However, in configurations where the CPI (31) and BTE processor (16) operate at different supply voltage levels, such as in the configuration of FIG. 4, the voltage level of the signals generated by the CPI (31) need to be converted to the voltage level of the BTE processor (16) and vice versa so as to ensure optimal communication between the devices. For example, the 3.0 volt signals transmitted by the CPI (31) may be converted to 2.0 volts so that the BTE processor (16) may process them. Likewise, the 2.0 volt signals transmitted by the BTE processor (16) may be converted to 3.0 volts so that the CPI (31) may process them.

In some examples, the programming cable (32; FIG. 3) is configured to perform voltage level translation between the CPI (31) and BTE processor (16). However, if the CPI (31) is used to program multiple BTE processors each operating at different voltage levels, this approach would require different programming cables to be used for each BTE processor.

Hence, in some examples, an off-the-shelf voltage level translator may be used to interface between the CPI (31) and BTE processor (16). Voltage level translators are also known as voltage or signal level shifters, signal level translators, and transceivers.

Figure 5:
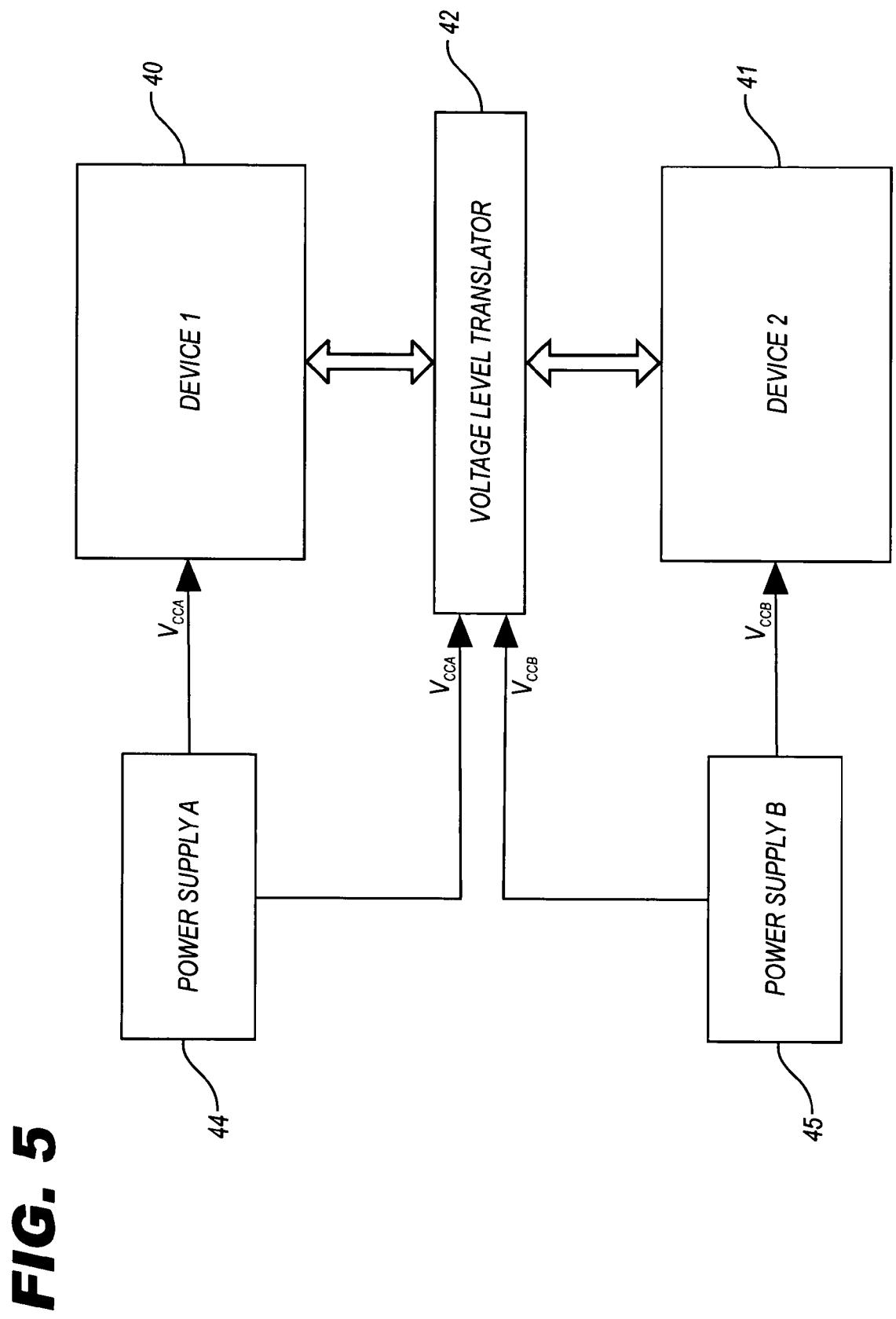
FIG. 5 illustrates an exemplary application wherein a voltage level translator is used to facilitate bidirectional voltage level translation between a first device and a second device according to principles described herein.

FIG. 5 illustrates an exemplary application wherein a voltage level translator (42) is used to facilitate bidirectional voltage level translation between a first device (40) and a second device (41). The first device (40) may include any electronic device such as, but not limited to, the CPI (31) of FIG. 4. Likewise, the second device (41) may include any electronic device such as, but not limited to, the BTE processor (16) of FIG. 4. As shown in FIG. 5, the first device (40) receives a supply voltage $V_{CCA}$ from a first power supply (44). Likewise, the second device (41) receives a supply voltage $V_{CCB}$ from a second power supply (45).

The voltage level translator (42) shown in FIG. 5 is configured to provide an interface such that the first and second devices (40, 41) can communicate one with another. As shown in FIG. 5, the voltage level translator (42) has two separate $V_{CC}$ supplies, one for each power supply (44, 45). Using circuitry known in the art, the voltage level translator (42) converts the signals from the first device (40) to signals having a voltage level of $V_{CCB}$ such that they may be processed by the second device (41). Likewise the voltage level translator (42) converts the signals from the second device (41) to signals having a voltage level of $V_{CCA}$ such that they may be processed by the first device (40).

The voltage level translator (42) of FIG. 5 may include any off-the-shelf component, custom integrated circuit, or combination of circuitry as best serves a particular application. An exemplary, but not exclusive, off-the-shelf voltage level translator (42) is the FXL4T245 Low Voltage Dual Supply 4-Bit Signal Translator manufactured by Fairchild Semiconductor™.

The voltage level translator (42) may be located within either device (40 or 41) as best serves a particular application. For example, the voltage level translator (42) may be located on a printed circuit board (PCB) assembly of which the BTE processor (16) of FIG. 4 is a part.

As mentioned, the voltage level translator (42) requires two $V_{CC}$ supplies, $V_{CCA}$ and $V_{CCB}$. However, if the voltage level translator (42) is located within one of the devices (e.g., the second device (41)), it may be difficult to provide the other supply voltage (e.g, $V_{CCA}$) to the voltage level translator (42).

For example, if the voltage level translator (42) is located within the BTE processor assembly (16; FIG. 3), is often difficult to transmit a power signal having a voltage level equal to $V_{CCA}$ from the CPI (31; FIG. 3) to the voltage level translator (42). The difficulty arises, in part, because of noise corruption, radio frequency (RF) interference, and/or signal degradation that occurs as the power signal travels along the programming cable (32; FIG. 3). The noise corruption, RF interference, and/or signal degradation may cause the transmitted power signal to have a different voltage level than the other data signals that are also transmitted from the CPI (31; FIG. 3) to the BTE processor (16; FIG. 3). Such variance in voltage levels between the signals may result in communication errors and/or device malfunction. Other difficulties associated with the transmission of a dedicated power signal include, but are not limited to, size constraints of the devices, the unavailability of connecting pins, and additional tooling costs.

Another possible method of providing $V_{CCA}$ to a voltage level translator (42) that is located within the second device (41) is to include an additional power supply within the second device (41). This additional power supply may then be configured to generate the required voltage $V_{CCA}$. However, a number of disadvantages are associated with this approach. First, an additional power supply requires additional components and occupies valuable PCB space within the second device (41). An additional power supply may also increase the overall power consumption of the second device (41). Moreover, the use of an additional power supply limits the devices with which the second device (41) can communicate to those that operate at the same voltage as the voltage output by the additional power supply.

The present methods and systems obviate the need for an additional power supply to be included within the second device (41) or for a dedicated power signal to be transmitted from the first device (40) to the second device (41). As will be described in more detail below, the supply voltage corresponding to the first device (40), $V_{CCA}$, may be automatically derived from one of the digital signals that is transmitted from the first device (40) to the second device (41). In this manner, communication may be facilitated between two devices even though one or more of their supply voltage levels is unknown.

Figure 6:
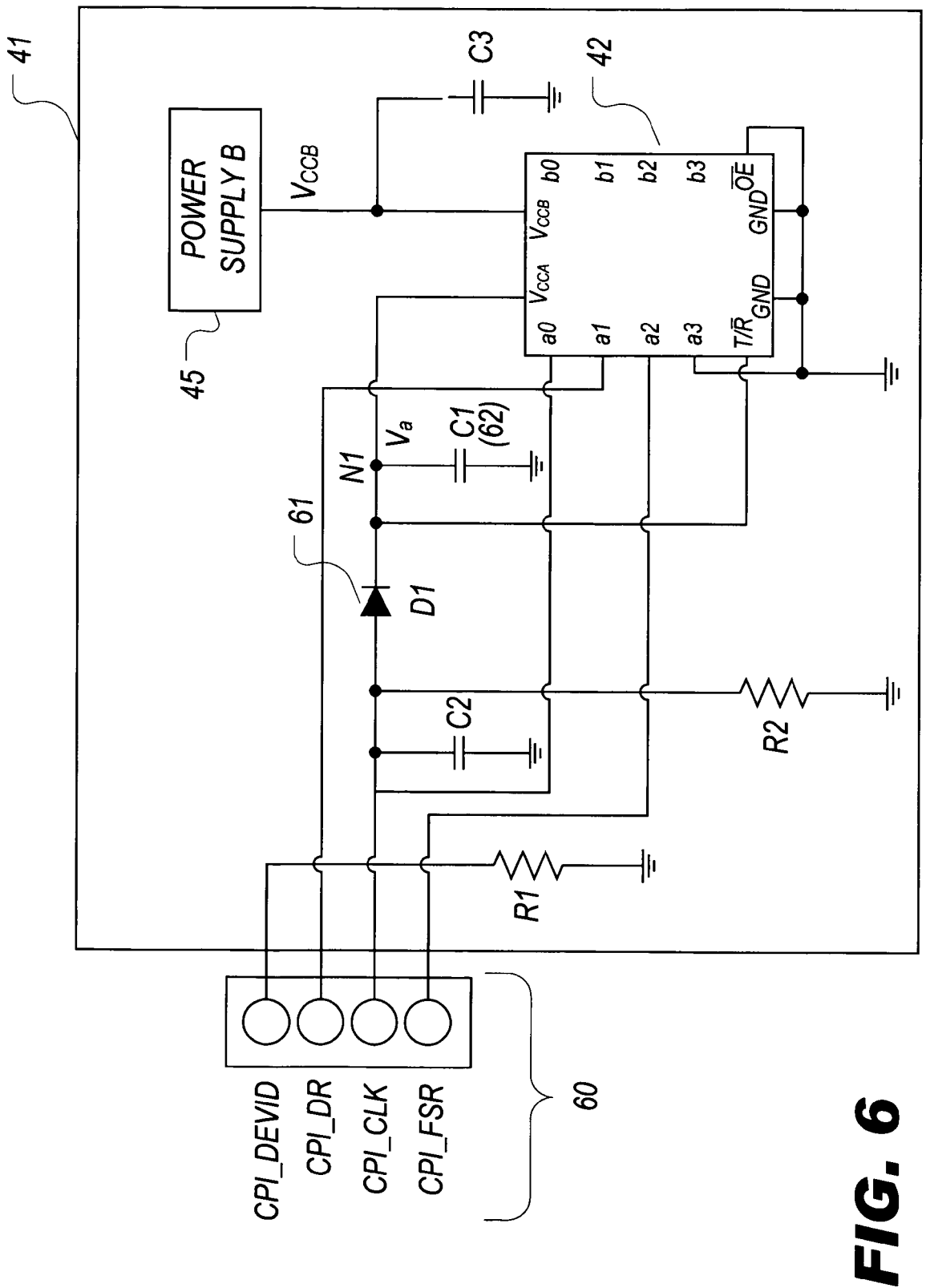
FIG. 6 illustrates an exemplary configuration wherein one of the supply voltages, $V_{CCA}$, required by the voltage level translator is derived from one of the digital signals transmitted from the first device to the second device according to principles described herein.

FIG. 6 illustrates an exemplary configuration wherein one of the supply voltages, $V_{CCA}$, required by the voltage level translator (42) is derived from one of the digital signals transmitted from the first device (40) to the second device (41). As shown in FIG. 6, the voltage level translator (42) is included within the PCB assembly of the second device (41). However, it will be recognized that the voltage level translator (42) may additionally or alternatively be included within the first device (40).

As shown in FIG. 6, one of the supply voltages required by the voltage level translator (42), $V_{CCB}$, may be provided by the power supply (45) of the second device (41). The other supply voltage required by the voltage level translator (42), $V_{CCA}$, is derived from one of the digital signals (60) transmitted from the first device (40) to the second device (41). For example, as shown in FIG. 6, $V_{CCA}$ may be derived from CPI_CLK, the digital clock signal transmitted from the CPI (31; FIG. 4) to the BTE processor (16; FIG. 4). However, it will be recognized that the supply voltage $V_{CCA}$ may be derived from any clock or other digital signal provided by the first device (40) as best serves a particular application.

As shown in FIG. 6, the clock signal CPI_CLK is input into a series diode D1 (61) followed by a capacitor C1 (62) that is connected to circuit ground. As will be explained below, the diode (61) and capacitor (62) combination produces a voltage $V_a$ which equals a logic voltage $V_{dd}$ of CPI_CLK less a forward voltage drop $V_{fd}$ of the diode (61).

To produce the voltage $V_a$, the diode (61) charges the capacitor (62) with the logic voltage $V_{dd}$ of the clock signal during the positive cycles of the clock signal. Because of the peak hold nature of the circuit diode (61) and capacitor (62), variations in duty cycle of the clock signal may be tolerated. The capacitor (62) may then supply the voltage level translator (42) with $V_a$ at the $V_{CCA}$ input of the voltage level translator (42).

The forward voltage drop $V_{fd}$ of the diode (61) is directly proportional to the current through the diode (61). Because the voltage level shifter (42) consumes very little current (e.g., 20 μA), the current that passes through the diode (61) is negligible. Hence, the forward voltage drop $V_{fd}$ across the diode (61) is also negligible and $V_a$ is approximately equal to $V_{dd}$.

In some examples, the diode (61) is a schottky diode. Schottky diodes are advantageous in many applications because they support high frequency clock signals and because their corresponding forward voltage drop $V_{fd}$ is lower than conventional diodes. However, it will be recognized that any type of diode may be used as the diode (61) as best serves a particular application.

The size of the capacitor (62) may vary as best determines a particular application and is determined by the speed and power requirements of the voltage level translator (42). An exemplary, but not exclusive, value for the capacitor (62) is substantially equal to or less than 1 microfarad (μF).

Additional capacitors and resistors may be used to decouple the incoming clock signal and/or to ensure that the derived voltage $V_a$ is low when the second device (41) is in standalone mode. For example, a capacitor C2 (63) having any suitable value (e.g., 15 pF) may be used to decouple the CPI_CLK signal at the incoming port. Additionally or alternatively, a resistor R2 (64) having any suitable value (e.g., 10 Kohm) may be used to pull down the CPI_CLK signal to ensure that the derived voltage $V_a$ is low when the second device (41) is in standalone mode.

Some voltage level translators (42) require the input supply voltages $V_{CCA}$ and $V_{CCB}$ to reach a predetermined operating voltage (e.g., 1.1 volts) before any valid serial communication can take place between the devices (40, 41). Hence, the diode (61) and capacitor (62) may be selected such that the derived voltage $V_a$ reaches the predetermined operating voltage level quickly enough (e.g., less than 60 ms) so as to ensure valid operation of the voltage level translator (42).

The configuration shown in FIG. 6 may be used for any logic voltage level $V_{dd}$ and is only constrained by the minimum and maximum power supply requirements of the voltage level translator (42). An exemplary voltage level translator (42) may allow the voltage supplies to range from approximately 1.1 volts to 3.6 volts. Hence, the configuration of FIG. 6 may be used to adapt to any supply voltage level of either the first or second devices (40, 41).

For example, the configuration of FIG. 6 may be used to facilitate communication between a CPI (31; FIG. 3) operating at 3.0 volts and a BTE processor (16; FIG. 3) operating at 2.0 volts. In addition, when either the CPI (31; FIG. 3) or the BTE processor (16; FIG. 3) is upgraded to a newer device that operates at a different supply voltage level (e.g., 2.7 volts), the same programming cable (32) may be used to facilitate communication therebetween because the circuitry shown in FIG. 6 is configured to adapt to a change in either of the devices' supply voltage levels.

In some examples, one or more additional voltage level translators (42) may be included within either the first or second devices (40, 41) to further facilitate transmission of data from the second device (41) to the first device (40). For example, a voltage level translator (42) may be included within both the first device (40) and the second device (41).

In some examples, the diode (61) and/or capacitor (62) may be integrated into the voltage level translator chip (42). In this manner, the voltage level translator chip (42) derives the required supply voltage internally.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
    a behind-the-ear signal processor configured to process an acoustic signal and generate one or more stimulation parameters based on the acoustic signal and configured to control an implantable cochlear stimulator, the behind-the-ear signal processor being configured to operate at a first supply voltage level;
    a clinician's programming interface configured to be coupled to the behind-the-ear signal processor and facilitate programming of the behind-the-ear signal processor, the clinician's programming device being configured to operate at a second supply voltage level that is different than the first supply voltage level;
    a voltage level translator circuit configured to facilitate communication between the behind-the-ear signal processor and the clinician's programming interface by converting digital signals that are transmitted from said clinician's programming interface to said behind-the-ear signal processor from the second supply voltage level to a voltage level substantially equal to the first supply voltage level, said conversion being based on a first input voltage signal into said translator circuit; and
    a circuit comprising a diode in series with a capacitor, the circuit comprising the diode in series with the capacitor configured to receive a digital signal included within the digital signals and generate said first input voltage signal by charging said capacitor to a voltage level that is substantially equal to a voltage level of said digital signal.

2. The system of claim 1, wherein said conversion is further based on a second input voltage signal into said translator circuit, wherein said second input voltage signal has a voltage level substantially equal to said first supply voltage level of said behind-the-ear signal processor.

3. The system of claim 1, wherein said digital signal comprises a clock signal generated by the clinician's programming interface.

4. The system of claim 1, wherein said diode is configured to charge said capacitor during a plurality of positive cycles of said digital signal.

5. The system of claim 1, wherein said capacitor is configured to supply said first input voltage signal to said translator circuit.

6. The system of claim 1, wherein said diode comprises a schottky diode.

7. The system of claim 1, wherein said circuit comprising the diode and the capacitor is included within said translator circuit.

8. The system of claim 1, wherein said voltage level translator circuit is further configured to convert a voltage level of one or more signals generated by said behind-the-ear signal processor to a voltage level substantially equal to the second supply voltage level of said clinician's programming interface.

9. The system of claim 1, wherein the voltage level translator circuit is located within an assembly of the behind-the-ear signal processor.

10. The system of claim 1, wherein the circuit comprising the diode and the capacitor is located within an assembly of the behind-the-ear signal processor.

11. A system comprising:
    a behind-the-ear signal processor configured to process an acoustic signal and generate one or more stimulation parameters based on the acoustic signal and configured to control an implantable cochlear stimulator, the behind-the-ear signal processor being configured to operate at a first supply voltage level;
    a clinician's programming interface configured to be coupled to the behind-the-ear signal processor and facilitate programming of the behind-the-ear signal processor, the clinician's programming device being configured to operate at a second supply voltage level that is different than the first supply voltage level;
    a voltage level translator circuit configured to facilitate communication between the clinician's programming interface and the behind-the-ear signal processor by converting digital signals that are transmitted from the behind-the-ear signal processor to the clinician's programming interface from the first supply voltage level to a voltage level substantially equal to the second supply voltage level, the conversion being based on a first input voltage signal into the translator circuit; and
    a circuit comprising a diode in series with a capacitor, the circuit comprising the diode in series with the capacitor configured to receive a digital signal included within the digital signals and generate the first input voltage signal by charging the capacitor to a voltage level that is substantially equal to a voltage level of the digital signal.

12. The system of claim 11, wherein said conversion is further based on a second input voltage signal into said first circuit, wherein said second input voltage signal has a voltage level substantially equal to said supply voltage level of said second device.

13. The system of claim 11, wherein said digital signal comprises a clock signal generated by the behind-the-ear signal processor.

14. The system of claim 11, wherein said diode is configured to charge said capacitor during a plurality of positive cycles of said digital signal.

15. The system of claim 11, wherein said diode comprises a schottky diode.

16. The system of claim 11, wherein said translator circuit is further configured to convert a voltage level of one or more signals generated by said clinician's programming interface to a voltage level substantially equal to the first supply voltage level of said behind-the-ear signal processor.

17. A method comprising:
providing a behind-the-ear signal processor configured to process an acoustic signal and generate one or more stimulation parameters based on the acoustic signal and configured to control an implantable cochlear stimulator, the behind-the-ear signal processor being configured to operate at a first supply voltage level;
providing a clinician's programming interface configured to be coupled to the behind-the-ear signal processor and facilitate programming of the behind-the-ear signal processor, the clinician's programming device being configured to operate at a second supply voltage level that is different than the first supply voltage level;
providing a voltage level translator circuit configured to convert digital signals that are transmitted from said clinician's programming interface to said behind-the-ear signal processor from the second supply voltage level to a voltage level substantially equal to the first supply voltage level, said conversion being based on a first input voltage signal into said translator circuit;
providing a circuit comprising a diode in series with a capacitor;
receiving, by the diode, a digital signal included within the digital signals; and
generating, by the diode and the capacitor, said first input voltage signal by charging said capacitor to a voltage level that is substantially equal to a voltage level of said digital signal.

18. The method of claim 17, wherein said conversion is further based on a second input voltage signal into said translator circuit, wherein said second input voltage signal has a voltage level substantially equal to said supply voltage level of said behind-the-ear signal processor.

19. The method of claim 17, wherein said digital signal comprises a clock signal generated by the clinician's programming interface.

20. The method of claim 17, further comprising charging said capacitor during a plurality of positive cycles of said digital signal.

* * * * *